US00PP20286P2

(12) United States Plant Patent
Dupont, Jr.

(10) Patent No.: US PP20,286 P2
(45) Date of Patent: Sep. 8, 2009

(54) ***RUDBECKIA* PLANT NAMED 'EARLY BIRD GOLD'**

(50) Latin Name: *Rudbeckia fulgida*
Varietal Denomination: Early Bird Gold

(75) Inventor: Robert J. Dupont, Jr., Plaquemine, LA (US)

(73) Assignee: Dupont Nursery, Inc., Plaquemine, LA (US)

( * ) Notice: Subject to any disclaimer, the term of this patent is extended or adjusted under 35 U.S.C. 154(b) by 0 days.

(21) Appl. No.: 12/217,751

(22) Filed: Jul. 7, 2008

(51) Int. Cl.
*A01H 5/00* (2006.01)

(52) U.S. Cl. ..... Plt./474
(58) Field of Classification Search ..... Plt./474
See application file for complete search history.

*Primary Examiner*—Kent L Bell
(74) *Attorney, Agent, or Firm*—C. A. Whealy

(57) ABSTRACT

A new and distinct cultivar of *Rudbeckia* plant named 'Early Bird Gold', characterized by its compact, upright to outwardly spreading and mounded plant habit; freely branching growth habit; freely flowering habit; single-type inflorescences with golden yellow-colored ray florets and dark brown-colored disc florets; and good garden performance.

2 Drawing Sheets

Botanical designation: *Rudbeckia fulgida.*
Cultivar denomination: 'EARLY BIRD GOLD'.

BACKGROUND OF THE INVENTION

The present invention relates to a new and distinct cultivar of *Rudbeckia* plant, botanically known as *Rudbeckia fulgida* and hereinafter referred to by the name 'Early Bird Gold'.

The new *Rudbeckia* is a naturally-occurring whole plant mutation of *Rudbeckia fulgida* 'Goldstrum', not patented. The new *Rudbeckia* was discovered and selected by the Inventor as a single flowering plant within a population of plants of 'Goldstrum' in a controlled greenhouse environment in Plaquemine, La. in June, 2005.

Asexual reproduction of the new *Rudbeckia* by tissue culture in a controlled greenhouse environment in Plaquemine, La. since Feb. 1, 2007 has shown that the unique features of this new *Rudbeckia* are stable and reproduced true to type in successive generations.

SUMMARY OF THE INVENTION

Plants of the new *Rudbeckia* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Early Bird Gold'. These characteristics in combination distinguish 'Early Bird Gold' as a new and distinct cultivar of *Rudbeckia:*

1. Compact, upright to outwardly spreading and mounded plant habit.
2. Freely branching growth habit.
3. Freely flowering habit.
4. Single-type inflorescences with golden yellow-colored ray florets and dark brown-colored disc florets.
5. Good garden performance.

Plants of the new *Rudbeckia* differ from plants of the parent, 'Goldstrum', in the following characteristics:

1. Plants of the new *Rudbeckia* are more compact than plants of 'Goldstrum'.
2. Plants of the new *Rudbeckia* have a longer flowering period than plants of 'Goldstrum'.
3. Plants of the new *Rudbeckia* are more freely flowering than plants of 'Goldstrum'.

Plants of the new *Rudbeckia* can be compared to plants of the *Rudbeckia* 'Black Beauty', disclosed in U.S. Plant Pat. No. 12,648. In side-by-side comparisons conducted in Plaquemine, La., plants of the new *Rudbeckia* differed from plants of 'Black Beauty' in the following characteristics:

1. Plants of the new *Rudbeckia* were more compact than plants of 'Black Beauty'.
2. Plants of the new *Rudbeckia* were more freely branching than plants of 'Black Beauty'.

BRIEF DESCRIPTION OF THE PHOTOGRAPHS

The accompanying photographs illustrate the overall appearance of the new *Rudbeckia.* These photographs show the colors as true as it is reasonably possible to obtain in colored reproductions of this type. Colors in the photographs may differ slightly from the color values cited in the detailed botanical description which accurately describe the colors of the new *Rudbeckia.*

The photograph on the first sheet comprises a side perspective view of a typical flowering plant of 'Early Bird Gold' grown in a container.

The photograph on the second sheet is a close-up view of typical inflorescences of 'Early Bird Gold'.

Plants used for the aforementioned photographs were grown in a polyethylene-covered greenhouse during the late winter/early spring in Plaquemine, La. and under conditions and practices which approximate those generally used in commercial *Rudbeckia* production. During the production of the plants, day temperatures ranged from 29° C. to 32° C. and night temperatures ranged from 24° C. to 29° C. Rooted young plants were planted in one-quart containers and had been growing for twelve weeks when the photographs were taken.

DETAILED BOTANICAL DESCRIPTION

The following observations and measurements describe plants grown in an outdoor nursery during the late spring and summer in Fort Worth, Tex. and under conditions and practices which approximate those generally used in commercial *Rudbeckia* production. Rooted young plants were planted in ground beds and had been growing for twelve weeks when the description was taken. In the following description, color references are made to The Royal Horticultural Society Colour Chart, 2001 Edition, except where general terms of ordinary dictionary significance are used.

Botanical classification: *Rudbeckia fulgida* 'Early Bird Gold'.

Parentage: Naturally-occurring whole plant mutation of *Rudbeckia fulgida* 'Goldstrum', not patented.

Propagation:

*Type.*—By tissue culture.

*Time to initiate roots.*—About two weeks at temperatures of 29° C.

*Time to produce a rooted young plants.*—About two months at temperatures of 22° C.

*Root description.*—Fibrous, medium thickness; white in color.

*Root habit.*—Moderate branching; moderately dense.

Plant description:

*Appearance.*—Herbaceous perennial; single-type potted *Rudbeckia*. Compact, upright to outwardly spreading and mounded plant habit. Strong and freely branching growth habit with about 12 to 15 lateral branches developing per plant each with numerous secondary branches; dense and bushy habit. Moderately vigorous growth habit.

*Plant height.*—About 33 cm.

*Plant width.*—About 38 cm.

*Lateral branches.*—Length: About 21.5 cm. Diameter: About 5.5 mm. Internode length: About 2 cm to 3 cm. Strength: Strong. Texture: Pubescent. Color: Close to 146A to 146C occasionally overlain with close to 187A.

Foliage description:

*Arrangement.*—Alternate, simple, sessile.

*Length.*—About 13 cm to 15 cm.

*Width.*—About 3.5 cm to 5 cm.

*Shape.*—Elliptic to lanceolate.

*Apex.*—Acute.

*Base.*—Attenuate.

*Margin.*—Serrated.

*Texture, upper and lower surfaces.*—Pubescent; rough.

*Venation pattern.*—Pinnate.

*Color.*—Developing foliage, upper surface: More green than 147A. Developing foliage, lower surface: Close to 147B. Fully expanded foliage, upper surface: Close to 147A; venation, close to 144A. Fully expanded foliage, lower surface: Close to 147B; venation, close to 147C.

Inflorescence description:

*Appearance.*—Single-type inflorescence form with ligulate-shaped ray florets and tubular disc florets. Inflorescences borne on terminal and axillary peduncles above and beyond the foliage. Disc and ray florets arranged acropetally on a capitulum.

*Fragrance.*—None detected.

*Flowering season.*—Long flowering period; plants flower from early spring to late fall in Plaquemine, La., flowering continuous during this period.

*Inflorescence longevity.*—Inflorescences last about two weeks on the plant; inflorescences persistent.

*Quantity of inflorescence.*—Freely flowering, inflorescences developing at every node.

*Inflorescence bud.*—Height: About 7 mm. Diameter: About 8 mm. Shape: Oblate. Color: Close to 146A.

*Inflorescence size.*—Diameter: About 6.5 cm. Depth (height): About 1.75 cm. Diameter of disc: About 1.75 cm. Receptacle height: About 1 cm. Receptacle diameter: About 9 mm.

*Ray florets.*—Shape: Ligulate to lanceolate. Orientation: Initially incurved, then upright, then perpendicular to the peduncle; apices reflexing with development. Length: About 3.75 cm. Width: About 7.5 mm. Apex: Emarginate. Base: Obtuse. Margin: Entire. Texture, upper and lower surfaces: Smooth, glabrous; velvety; longitudinally ridged. Number of ray florets per inflorescence: About 13 to 17 arranged in a single whorl. Color: When opening, upper surface: Close to 17A. When opening, lower surface: Close to 15A. Fully opened, upper surface: More intense than 17A; venation, similar to lamina. Fully opened, lower surface: Close to 15A; venation, similar to lamina.

*Disc florets.*—Arrangement: Massed at center of receptacle. Shape: Tubular, elongated. Apex: Five-pointed. Length: About 7 mm. Width: About 1.5 mm. Number of disc florets per inflorescence: Numerous. Color, immature: Towards the apex, close to 200A; towards the base, close to 154D. Color, mature: Towards the apex, close to 200A; towards the base, close to 144A.

*Phyllaries.*—Number of phyllaries per inflorescence: About 14 to 17 in one to two whorls. Length: About 1.75 cm. Width: About 6 mm. Shape: Lanceolate. Apex: Mucronate. Base: Fused. Margin: Entire. Texture, upper surface: Smooth, glabrous. Texture, lower surface: Scattered pubescence. Color, upper surface: Close to 147A. Color, lower surface: Close to 147B.

*Peduncles.*—Length, terminal peduncle: About 8 cm. Length, fourth peduncle: About 10 cm. Diameter: About 4 mm. Angle: Erect to about 55° from vertical. Strength: Moderately strong, flexible. Texture: Pubescent; longitudinally ridged. Color: Close to 146A to 146C occasionally overlain with close to 187A.

*Reproductive organs.*—Androecium: Quantity per disc floret: Five. Filament length: About 1 mm. Filament color: Close to 145D. Anther shape: Oblong. Anther length: About 1 mm. Anther color: Close to 6A. Pollen amount: None observed. Gynoecium (present only on disc florets). Pistil length: About 7 mm. Stigma shape: Two-parted. Stigma color: Close to 154C. Style length: About 3 mm. Style color: Close to 154C.

*Seed/fruit.*—Seed and fruit production has not been observed. Disease/pest resistance: Resistance to pathogens and pests common to *Rudbeckias* has not been observed on plants grown under commercial conditions.

Garden performance: Plants of the new *Rudbeckia* have been observed to have good garden performance and to tolerate wind, rain and temperatures from about 1° C. to about 35° C.

It is claimed:

1. A new and distinct *Rudbeckia* plant named 'Early Bird Gold' as illustrated and described.

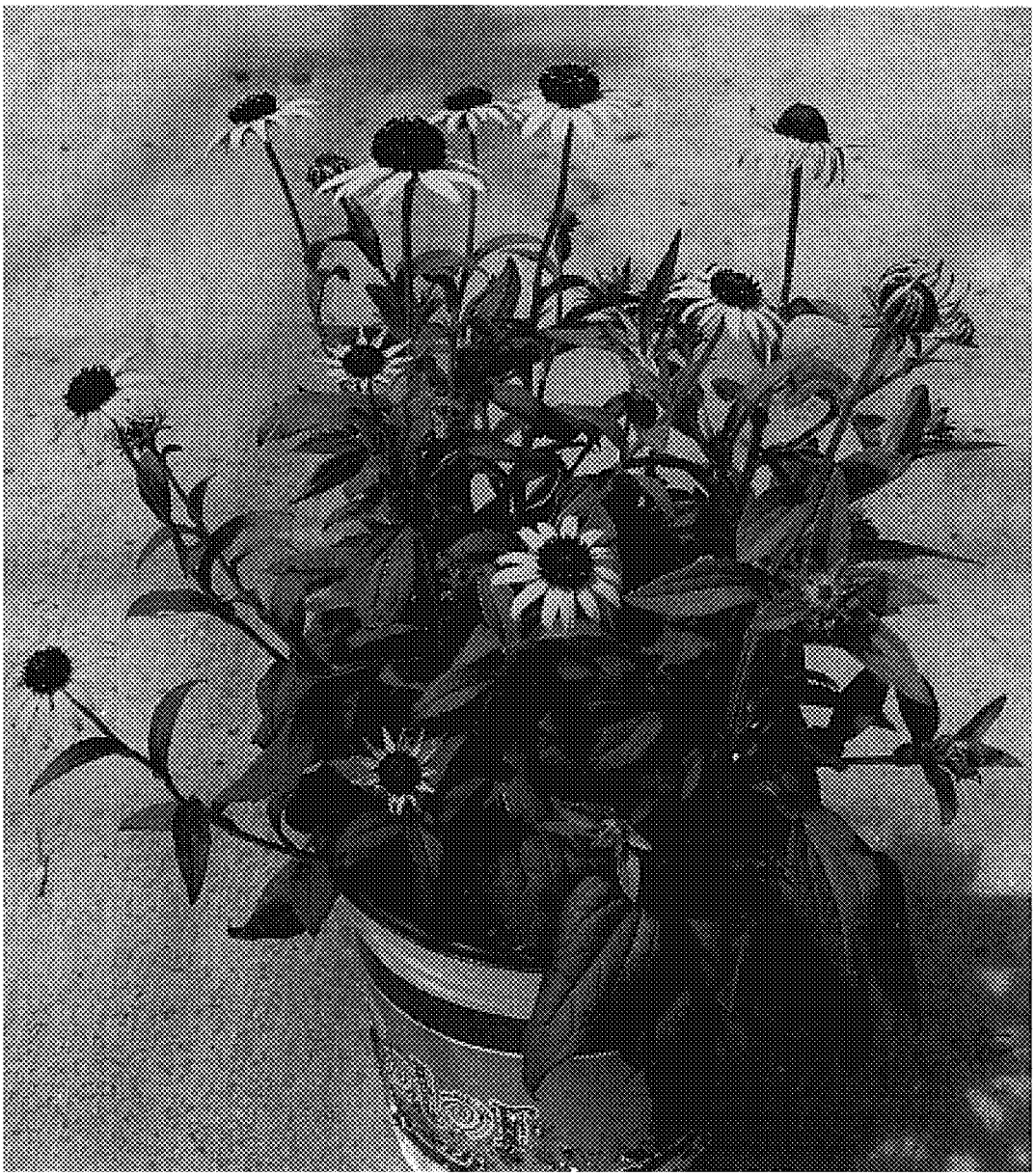

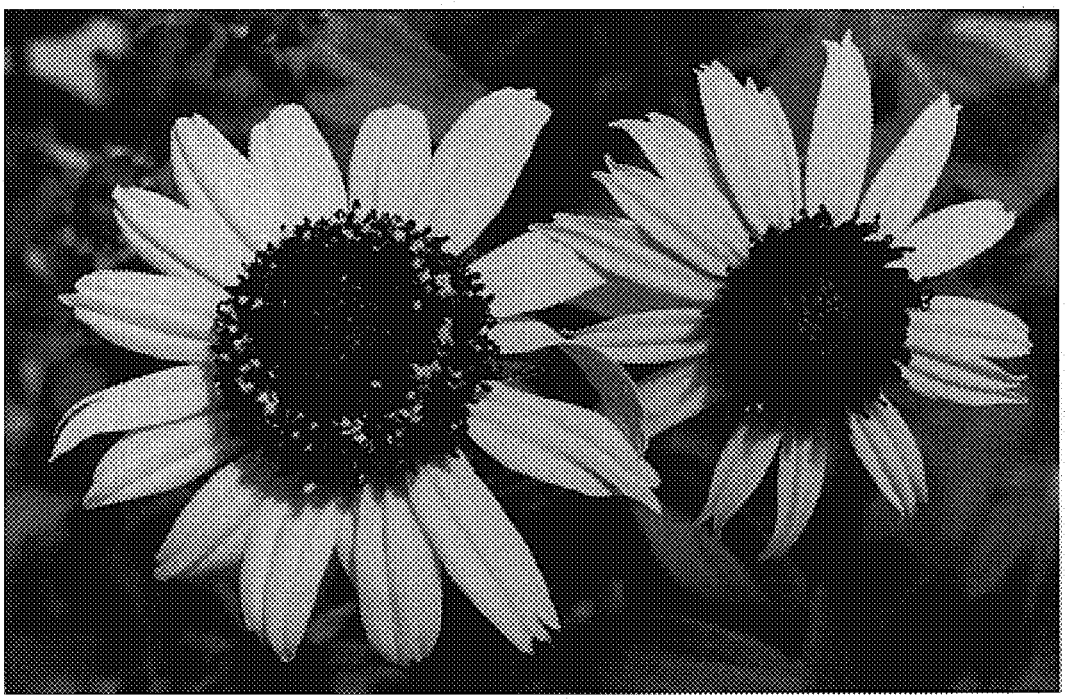

* * * * *